(12) United States Patent
Weinstat

(10) Patent No.: US 8,631,808 B1
(45) Date of Patent: Jan. 21, 2014

(54) BEVELED TOOTHPICK

(76) Inventor: Marvin Cary Weinstat, Corte Madera, CA (US)

( * ) Notice: Subject to any disclaimer, the term of this patent is extended or adjusted under 35 U.S.C. 154(b) by 0 days.

(21) Appl. No.: 13/373,351

(22) Filed: Nov. 10, 2011

(51) Int. Cl.
*A61C 15/00* (2006.01)

(52) U.S. Cl.
USPC .......................................... 132/329; 132/321

(58) Field of Classification Search
USPC ................................. 132/321, 329
See application file for complete search history.

(56) References Cited

U.S. PATENT DOCUMENTS

| | | | | |
|---|---|---|---|---|
| 361,775 A | * | 4/1887 | Nellis ............................ | 132/329 |
| 3,978,872 A | * | 9/1976 | Bond ............................ | 132/329 |
| 4,651,760 A | * | 3/1987 | Reipur .......................... | 132/329 |
| 4,660,583 A | * | 4/1987 | Brown .......................... | 132/329 |
| 5,234,009 A | * | 8/1993 | Lemon et al. ................. | 132/329 |
| 7,264,005 B2 | * | 9/2007 | Wong ............................ | 132/321 |

* cited by examiner

*Primary Examiner* — Rachel Steitz
(74) *Attorney, Agent, or Firm* — Risto A. Rinne, Jr.

(57) ABSTRACT

An apparatus for intrasulcular cleaning and dental maintenance includes a toothpick preferably made from a non-splintering wood. A first end of the toothpick includes a sloping (i.e., beveled) curvature that extends below a center longitudinal axis of the toothpick and terminates at a thin rounded tip. The rounded tip includes a radius designed for ease and comfort once inserted within a gingival sulcus between a tooth and a gum. The second end of the toothpick may include any desired shape. One or more grooves or geometric shapes are provided to help properly orient the toothpick and provide a tactile indication that the toothpick is properly oriented. The user traces around the tooth with the rounded tip to remove plaque and food debris. The toothpick may disposable or reusable and packaged together or individually wrapped.

16 Claims, 3 Drawing Sheets

BEVELED TOOTHPICK

RESERVATION OF RIGHTS

A portion of the disclosure of this patent document contains material which is subject to intellectual property rights such as but not limited to copyright, trademark, and/or trade dress protection. The owner has no objection to the facsimile reproduction by anyone of the patent document or the patent disclosure as it appears in the Patent and Trademark Office patent files or records but otherwise reserves all rights whatsoever.

BACKGROUND OF THE INVENTION

1. Field of the Invention

The present invention, in general, relates to dental maintenance and, more particularly, to a tool used for cleaning the gingival sulcus or intrasulcular cleaning of a space between a tooth and a gum, below the gum line.

Toothpicks, are in general, known. They are widely used and commonly available in many eating establishments such as restaurants and diners.

Toothpicks are meant to be used as a quick and convenient tool for cleaning food and other debris from in between the teeth and gums. They are inexpensive to manufacture and are typically offered for free to dining patrons.

However, the use of a toothpick presents potential for damage to the gums as toothpicks typically include a pointed tip. The pointed tip is sharp and may damage and cut the gum attachment which may cause the gums to bleed. Alternately, a person may apply too much pressure to the toothpick and the pointed tip may break off and become stuck between the teeth.

The conical shape of the pointed tip is narrow to allow easy insertion in between the teeth interdentally. However, the pointed tip is not well suited for placement under the gum line as it may cause damage to the connective tissues.

Dental floss is another tool used for cleaning of the space between teeth and the gum. Dental floss is a woven thread material that is grasped by both hands and placed in the space between two teeth. The dental floss is moved in an up and down direction to loosen food, plaque and debris that may become lodged between the teeth.

The use of dental floss is a less-convenient way to clean the spaces between the teeth. Using dental floss is more time consuming to clean the teeth and therefore lessens the user's desire to regularly clean their teeth and gums.

Dental floss is also difficult to maneuver once placed in the mouth of the user. Since dental floss requires two hands to hold each end, it is sometimes difficult to reach teeth (i.e., molars) that are located at a rear of the mouth. Cleaning with dental floss is usually accomplished over a sink and, unlike toothpicks, is seldom done in public.

Dental floss and regular conical toothpicks can be ineffective in removing plaque in certain areas which are generally unreachable by a person cleaning his or her own teeth. Currently-available personal dental maintenance activities are insufficient. This can lead to more frequent scheduling of appointments with a dentist to remove the aforementioned debris and plaque that flossing and use of a prior art type of toothpick have left behind.

Accordingly, there exists today a need for a beveled toothpick that helps to ameliorate the above-mentioned problems and difficulties as well as ameliorate those additional problems and difficulties as may be recited in the "OBJECTS AND SUMMARY OF THE INVENTION" or discussed elsewhere in the specification or which may otherwise exist or occur and that are not specifically mentioned herein.

As various embodiments of the instant invention help provide a more elegant solution to the various problems and difficulties as mentioned herein, or which may otherwise exist or occur and are not specifically mentioned herein, and by a showing that a similar benefit is not available by mere reliance upon the teachings of relevant prior art, the instant invention attests to its novelty. Therefore, by helping to provide a more elegant and effective solution to various needs, some of which may be long-standing in nature, the instant invention further attests that the elements thereof, in combination as claimed, cannot be obvious in light of the teachings of the prior art to a person of ordinary skill and creativity.

Clearly, such an apparatus for intrasulcular dental maintenance would be useful and desirable.

2. Description of Prior Art

Toothpicks are, in general, known. For example, the following patent documents describe various types of these devices, some of which may have some degree of relevance to the invention. Other patent documents listed below may not have any significant relevance to the invention. The inclusion of these patent documents is not an admission that their teachings anticipate any aspect of the invention. Rather, their inclusion is intended to present a broad and diversified understanding regarding the current state of the art appertaining to either the field of the invention or possibly to other related or even distal fields of invention.

U.S. Pat. No. 5,704,388 to Freeman, that issued on Jan. 6, 1998; and

U.S. Pat. No. 656,479 to Schellenbach, that issued on Aug. 21, 1900;

And including U.S. Design patents:

U.S. Design Pat. No. D523,992 to Le, that issued on Jun. 27, 2006;

U.S. Design Pat. No. D507,380 to Le, that issued on Jul. 12, 2005;

U.S. Design Pat. No. D437,459 to Inaba, that issued on Feb. 6, 2001; and

U.S. Design Pat. No. D382,368 to Hsu, that issued on Aug. 12, 1997.

While the structural arrangements of the above described devices may, at first appearance, have similarities with the present invention, they differ in material respects. These differences, which will be described in more detail hereinafter, are essential for the effective use of the invention and which admit of the advantages that are not available with the prior devices.

OBJECTS AND SUMMARY OF THE INVENTION

It is an object of the present invention to provide a beveled toothpick that is preferably made of a non-splintering wood.

It is also an important object of the invention to provide a beveled toothpick that is made from any desired material other than wood.

Another object of the invention is to provide a beveled toothpick that is useful for gingival sulcus or intrasulcular cleaning of a space between a tooth and a gum.

Still another object of the invention is to provide a beveled toothpick that includes a first end that includes a planar sloping curvature which extends below a center longitudinal axis of the toothpick.

Still yet another object of the invention is to provide a beveled toothpick that includes a rounded tip at a first end thereof.

Yet another important object of the invention is to provide a beveled toothpick that includes a rounded tip that is designed for optimal insertion under a gum line.

A first continuing object of the invention is to provide a beveled toothpick that includes one or a plurality of bevel orienting grooves ensure that the toothpick is oriented in a proper position.

A second continuing object of the invention is to provide a beveled toothpick that includes one or a plurality of bevel orienting grooves that provide an indication of where a user should grasp the toothpick.

A third continuing object of the invention is to provide a beveled toothpick that helps prevent gum disease and subsequent tooth loss.

A fourth continuing object of the invention is to provide a beveled toothpick that is disposable.

A fifth continuing object of the invention is to provide a beveled toothpick that is reusable.

A sixth continuing object of the invention is to provide a beveled toothpick that is inexpensive.

Briefly, a beveled toothpick that is constructed in accordance with the principles of the present invention is preferably made from a non-splintering wood. If desired, materials other than wood such as plastic or other composite materials may be used to form the toothpick. The toothpick is designed for intrasulcular cleaning of a space between a tooth and a gum. The toothpick includes a main body that includes a longitudinal length that is small-enough for insertion into a mouth of a user. A first end of the toothpick includes a sloping (i.e., beveled) curvature that extends below a center longitudinal axis of the toothpick. A conical end portion is provided by the sloping curvature located below the center longitudinal axis. The conical end portion includes a thin rounded tip with a radial shape that is designed for ease and comfort once inserted below the gum. An opposite second end of the toothpick may include a similar or any other desired shape. For example, it may be blunt. At least one groove or geometric shape is included proximate the sloping curvature. The groove or geometric shape are used to help properly orient the toothpick within the mouth of the user. If desired, more than one groove or geometric shape may be included. The grooves or geometric shapes provide a means for providing a tactile indication that the user has the toothpick properly oriented prior to use. The grooves or geometric shapes also provide a gripping surface for the user to grasp while holding the toothpick. To use the beveled toothpick, the conical end portion is placed over the tooth enamel. The rounded tip is then urged into the space between the tooth and the gum, commonly known as a gingival sulcus in the dentistry arts. The gingival sulcus is an area below the gum that harbors plaque that starts gingivitis and periodontitis. The user traces the gingival sulcus area around the tooth with a working surface of the rounded tip of the beveled toothpick. As the rounded tip is within the gingival sulcus, any plaque or lodged food debris is loosened and removed during cleaning. The beveled toothpick may be designed for one-time use (i.e., disposable) or the beveled toothpick may be reusable. If desired, multiple beveled toothpicks may be packaged together or they may be individually wrapped.

DETAILED DESCRIPTION OF THE INVENTION

Figure 1:
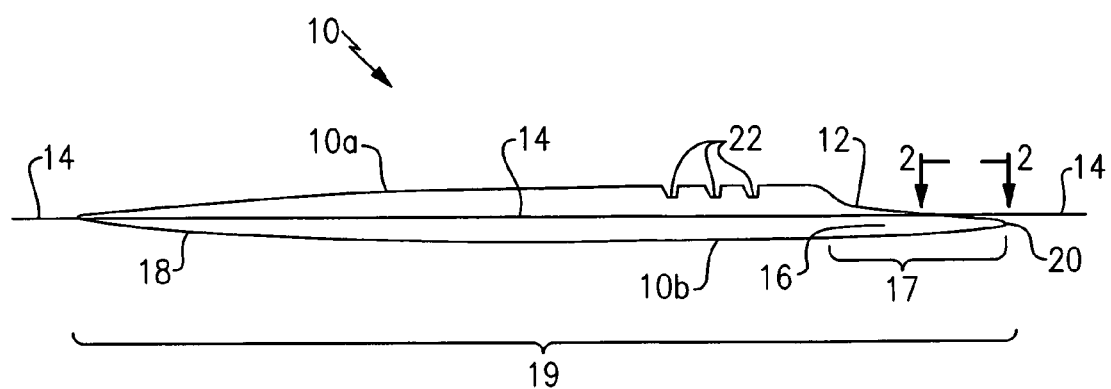
FIG. 1 is a side view of a beveled toothpick.

Referring on occasion to all of the FIGURE drawings and now, in particular to FIG. 1, is shown a beveled toothpick, identified in general, by the reference numeral 10.

The reader will notice that reference is occasionally made throughout the DETAILED DESCRIPTION OF THE INVENTION suggesting that the reader refer to a particular drawing FIGURE. The suggestion is at times made when the introduction of a new element requires the reader to refer to a different drawing FIGURE than the one currently being viewed and also when the timely viewing of another drawing FIGURE is believed to significantly improve ease of reading or enhance understanding. To promote rapid understanding of the instant invention the reader is encouraged to periodically refer to and review each of the drawing FIGURES for possible cross-referencing of component parts and for other potentially useful information.

Certain examples are shown in the above-identified FIGURES and are described in greater detail below. In describing these examples, like or identical reference numerals may be used to identify common or similar elements.

The beveled toothpick 10 is preferably comprised of a non-splintering wood. It is desired that the wood not break during use as the beveled toothpick 10 is to be inserted into a mouth of a user (not shown). The beveled toothpick 10 can be used with square or round toothpick stock.

If desired, the beveled toothpick 10 may be comprised of a molded plastic or other desired composite material instead of using wood to form the beveled toothpick 10.

The beveled toothpick 10 includes a small size (i.e., longitudinal length) to allow easy insertion inside the mouth. The small size also is permits the beveled toothpick 10 to be compact for storage and travel. The beveled toothpick 10 may be individually wrapped or a plurality of the beveled toothpicks 10 may be packaged together. The beveled toothpick 10 is comparable in overall size with a conventional prior art toothpick (not shown). If desired and to promote easier access and use in the mouth, the beveled toothpick 10 can be approximately one-half the overall longitudinal length of the conventional prior art toothpick. A shorter (i.e., one-half length) version would include an above the gum line polishing end (i.e., a blunt end) and the periodontal intrasulcular functional end, as described hereinafter.

The beveled toothpick 10 includes a sloping (i.e., beveled) curvature 12. The sloping curvature 12 extends (i.e., is flat) across the beveled toothpick 10. The sloping curvature 12 begins on an upper surface 10*a* of the beveled toothpick 10 and extends downward toward a lower surface 10*b*. The sloping curvature 12 terminates at a position below a center longitudinal axis 14 of the beveled toothpick 10. The lower surface 10*b* of the beveled toothpick 10 does not include the sloping curvature 12.

The upper surface 10*a* and the lower surface 10*b* together comprise an exterior surface of the beveled toothpick 10.

The sloping curvature 12 is provided on a first end 16 of the beveled toothpick 10. The first end 16 includes a conical end portion, identified by bracket 17. The conical end portion 17 generally includes a conical shape. The sloping curvature 12 removes some additional material of the beveled toothpick 10 from the conical end portion 17. Benefits of the sloping curvature 12 and the conical end portion 17 will be described in greater detail, hereinafter.

A second end 18 is located on an opposite side of the beveled toothpick 10. The second end 18 is disposed on an opposite side of the longitudinal length of a main body, identified by bracket 19, of the beveled toothpick 10. The main body 19 includes the entire longitudinal length between the conical end portion 17 of the first end 16 to the second end 18 of the beveled toothpick 10.

The opposite second end 18 may include an identical shape as on the first end 16 (i.e., the conical end portion 17) or any preferred shape or the second end 18 may include a blunt or pointed end, as shown. The second end 18 may also include a wider diameter than the first end 16, if desired.

A thin rounded tip 20 is included at a lowest point of the sloping curvature 12 below the center longitudinal axis 14 at the first end 16. The rounded tip 20 will be described in greater detail, hereinafter.

A plurality of grooves 22 are included on the upper surface 10a of the beveled toothpick 10. Any desired number of grooves 22 (one or more) may be included on the upper surface 10a of the beveled toothpick 10.

The grooves 22 are used to help properly orient the beveled toothpick 10 within the mouth of the user. The grooves 22 serve as a tactile indication that the user has the sloping curvature 12 of the beveled toothpick 10 facing toward a tooth 26. The grooves 22 also provide a gripping surface for the user to grasp while holding the beveled toothpick 10.

Figure 4:
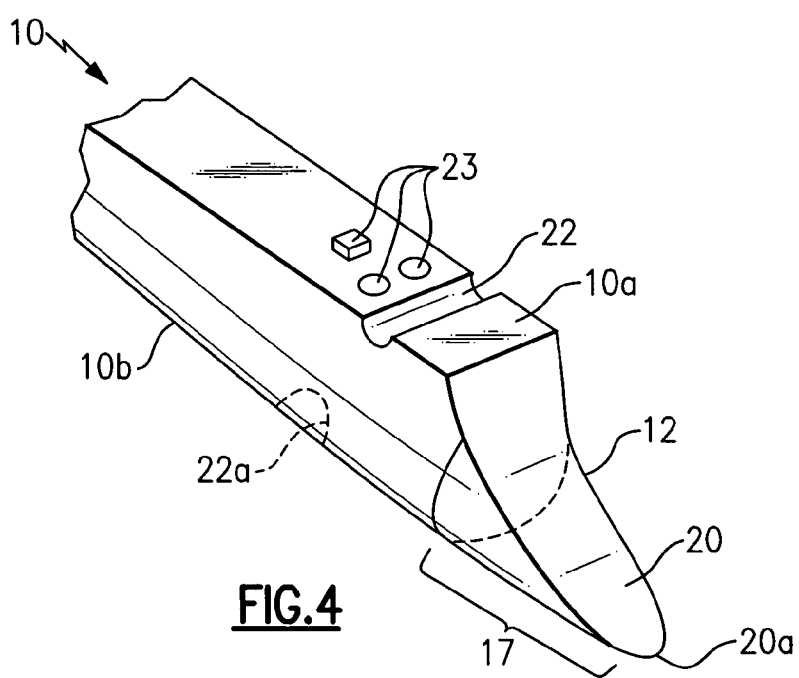
FIG. 4 is a view in perspective of a functional end of the beveled toothpick of FIG. 1.

If desired, a modified groove or grooves 22a (FIG. 4) could be included on the opposite lower surface 10b. The grooves 22 or the modified grooves 22a can be cut, impressed, molded, burned or etched into the main body 19 of the beveled toothpick 10. Other ways are possible to indicate by tactile feel the position of beveled toothpick 10. For example, raised or recessed geometric shapes 23 could be included for this purpose, where desired on the beveled toothpick 10. The user can feel, without having to view, the grooves 22, the modified grooves 22a or the geometric shapes 23 by making contact with their thumb or finger and, in this way, properly orient the beveled toothpick 10 for use.

The grooves 22, the modified grooves 22a, or the geometric shapes 23 all provide a means for providing a tactile indication of an orientation of the beveled toothpick 10.

Figure 2:
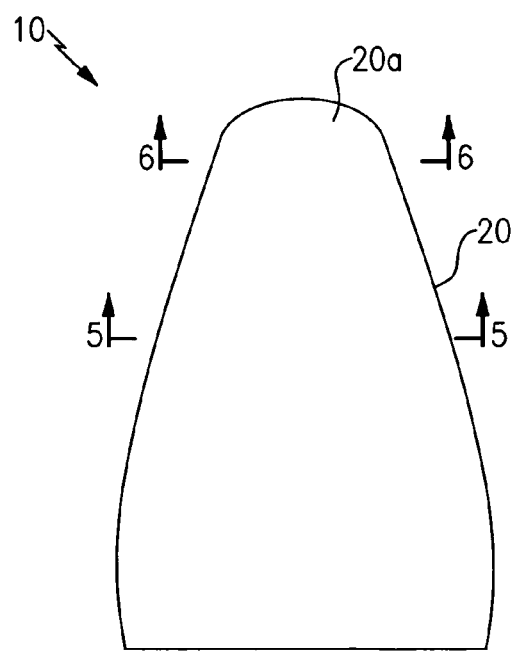
FIG. 2 is a top-elevational view taken along line 2-2 of a rounded tip of the beveled toothpick of FIG. 1.

Now referring to FIG. 2, is shown a top-elevational view of the rounded tip 20 of the conical end portion 17 taken along line 2-2 of FIG. 1.

The rounded tip 20 includes a curvature or rounded tip that is absent from prior art types of toothpicks (not shown). Prior art toothpicks include a pointed tip. The pointed tip creates a sharp point on the prior art toothpick. If not used with extreme care, the sharp point of the prior art toothpick may damage the user's gum tissue. It can also damage the connective tissue that attaches a gum 24 to the tooth 26.

It is important that the sloping curvature 12 of the conical end portion 17 extend to a location that is below the center longitudinal axis 14. If the sloping curvature 12 does not extend below the center longitudinal axis 14, as may be found on the prior art toothpick, a tip of the prior art toothpick would be thick and it would still include the point. The point would have the disadvantages previously mentioned and it would be especially weak and subject to breakage while disposed under the gum 24. Alternately, if the point is ground off or otherwise removed from the prior art toothpick with the sloping curvature 12 ending above the center longitudinal axis 14, the tip would be blunt and thick and unsuitable for placement under the gum 24.

An unexpected benefit is also provided by the conical end portion 17 of the beveled toothpick 10. As the rounded tip 20 is located on the sloping curvature 12 of the conical end portion 17, less wood is present at the location of where the rounded tip 20 is provided. This provides a thin working surface 20a that can easily be inserted under the gum 24 into a sulcus. Unlike the prior art toothpicks, the working surface 20a is not sharp (i.e., it is curved) and is much less likely to cause damage (i.e., cuts or damage) to the gum 24 or connective tissues.

Figure 3:
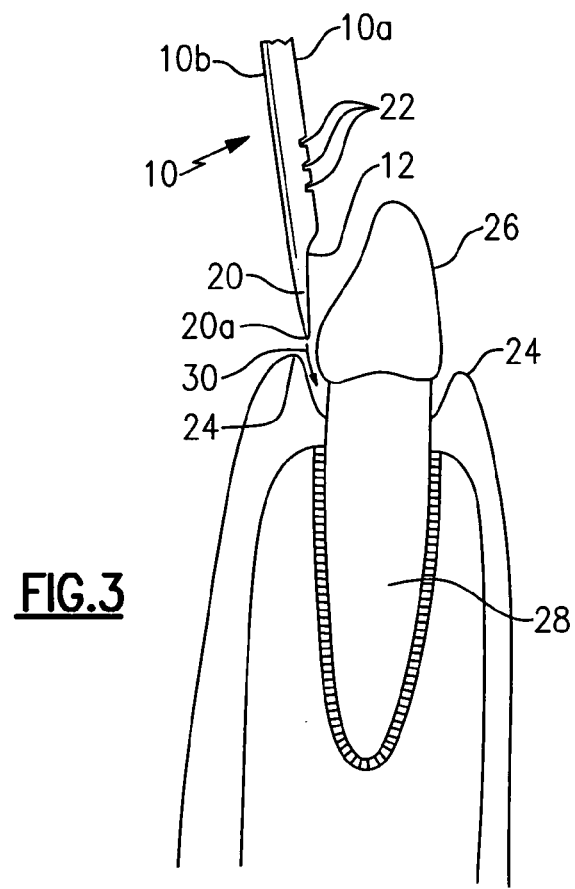
FIG. 3 is partial view of the beveled toothpick of FIG. 1 prior to insertion within a gingival sulcus between a tooth and a gum.

Now referring to FIG. 3, the gum 24 is shown surrounding the tooth 26. The tooth 26 has an enamel covering over dentin 28.

The gum 24 has been pulled slightly away from the tooth 26 for clarity. The space between the gum 24 and the tooth 26 is called a gingival sulcus. The beveled toothpick 10 is designed for optimal intrasulcular cleaning of the gingival sulcus.

To use the beveled toothpick 10 for cleaning a lower tooth 26, the upper surface 10a is oriented to be facing upward and the user places a finger or thumb on the grooves 22 (or the geometric shapes 23). The user grasps the beveled toothpick 10 in a manner similar to that of holding a pencil or pen.

The user then opens their mouth a sufficient amount to permit access of the beveled toothpick 10 to a desired tooth 26. The user places the beveled toothpick 10 in an elevated and slightly angled position with respect to the desired tooth 26 that is to be cleaned. The working surface 20a of the rounded tip 20 is urged downward in the gingival sulcus area between the gum 24 and the tooth 26, as shown by arrow 30.

The user lightly traces around the tooth 26 under the gum 24 with the working surface 20a of the beveled toothpick 10. The beveled toothpick 10 removes plaque that is present within the gingival sulcus. This action is repeated on each tooth 26 within the mouth of the user. The beveled toothpick 10 is inverted for cleaning the upper teeth.

With routine regular use of the beveled toothpick 10, especially after meals, risk of gingivitis and other gum diseases (i.e., periodontitis) will likely be reduced. Cleaning of the gingival sulcus is an important aspect of dental maintenance and use of the beveled toothpick 10 provides a quick and convenient method to accomplish proper removal of plaque from under the gum 24.

Figure 5:
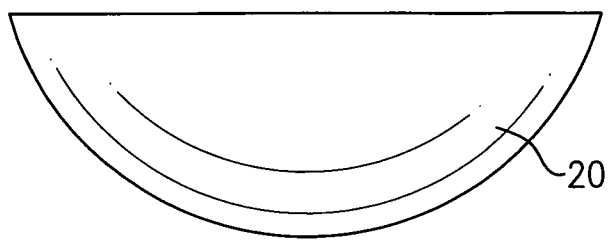
FIG. 5 is a cross-sectional view taken along line 5-5 of the rounded tip of FIG. 2.
Figure 6:
FIG. 6 is a cross-sectional view taken along line 6-6 of the rounded tip of FIG. 2.

Now referring to FIGS. 5 and 6, two cross-sectional views taken at two different locations on the rounded tip 20 of FIG. 2 are shown.

FIG. 5 shows a cross-sectional view away from the working surface 20a of the rounded tip 20.

FIG. 6 shows a cross-sectional view taken near the working surface 20a of the rounded tip 20.

As can be seen, the thickness of the beveled toothpick 10 along the sloping curvature 12 becomes thinner and thinner toward the working surface 20a of the rounded tip 20. A thin and naturally rounded termination is provided for the rounded tip 20 by extending the sloping curvature 12 below the center longitudinal axis 14.

The invention has been shown, described, and illustrated in substantial detail with reference to the presently preferred embodiment. It will be understood by those skilled in this art that other and further changes and modifications may be made without departing from the spirit and scope of the invention which is defined by the claims appended hereto.

What is claimed is:

1. A toothpick, comprising:
   (a) a main body that includes a longitudinal length and wherein said main body includes a first end and an opposite second end, and wherein said main body is not hollow, and wherein, during manufacture of said toothpick, said first end includes a conical shape, thereto, and wherein, during further manufacture, additional material is removed from said conical end; and
   (b) wherein, during said further manufacture, a sloping curvature that begins a predetermined distance away from said first end at an upper exterior surface of said main body is provided, and wherein said sloping curvature progressively extends deeper into said main body toward an opposite bottom surface of said conical shaped first end as said sloping curvature progressively extends toward said first end, wherein said sloping curvature terminates at said first end and at said opposite bottom surface of said conical shaped first end to provide a termination of said first end, and wherein said additional material that is removed from said first end includes all of said conical shaped first end that is disposed above said sloping curvature, and wherein said sloping curvature extends across a width of said main body, and wherein said termination of said first end is disposed below a longitudinal center axis of said main body, and wherein said termination of said first end includes an arcuate shape that extends across a width of said main body along where said sloping curvature and said opposite bottom surface of said conical shaped first end intersect, and wherein said arcuate shape includes an edge that extends along an entire length of said termination of said first end, wherein said termination of said first end of said toothpick includes a rounded end, and wherein an entire length of said edge includes said arcuate shape, and wherein said edge is able to enter a gingival sulcus without puncturing a tissue that said edge contacts at a base of said gingival sulcus.

2. The toothpick of claim 1 wherein said first end includes a rounded working surface.

3. The toothpick of claim 1 wherein said main body is round in cross-section.

4. The toothpick of claim 1 wherein said main body is made of wood.

5. The toothpick of claim 1 wherein said main body is formed of a plastic or composite material.

6. The toothpick of claim 1 wherein said main body is square in cross-section.

7. The toothpick of claim 1 wherein said toothpick includes a raised or recessed geometric shape that provides a tactile indication of an orientation of said toothpick, said means for providing a tactile indication disposed on said exterior surface of said main body.

8. The toothpick of claim 1 wherein said second end includes a desired termination.

9. The toothpick of claim 8 wherein said desired termination includes a blunt end.

10. A toothpick, comprising:
    (a) a main body that includes a longitudinal length and wherein said main body includes a first end and an opposite second end, and wherein said main body is not hollow, and wherein, during manufacture of said toothpick, said first end includes a conical shape, thereto, and wherein, during further manufacture, additional material is removed from said conical end;
    (b) a raised or recessed geometric shape that provides a tactile indication of an orientation of said toothpick, said means for providing a tactile indication disposed on an exterior surface of said main body; and
    wherein during said further manufacture, a sloping curvature that begins a predetermined distance away from said first end at an upper exterior surface of said main body is provided, and wherein said sloping curvature progressively extends deeper into said main body toward an opposite bottom surface of said conical shaped first end as said sloping curvature progressively extends toward said first end, wherein said sloping curvature terminates at said first end and at said opposite bottom surface of said conical shaped first end to provide a termination of said first end, and wherein said additional material that is removed from said first end includes all of said conical shaped first end that is disposed above said sloping curvature, and wherein said sloping curvature extends across a width of said main body, and wherein said at termination of said first end is disposed below a longitudinal center axis of said main body, and wherein said termination of said first end includes an arcuate shape that extends across a width of said main body along where said sloping curvature and said opposite bottom surface of said conical shaped first end intersect, and wherein said arcuate shape includes an edge that extends along an entire length of said termination of said first end, wherein said termination of said first end of said toothpick includes a rounded end, and wherein an entire length of said edge includes said arcuate shape, and wherein said edge is able to enter a gingival sulcus without puncturing a tissue that said edge contacts at a base of said gingival sulcus.

11. The toothpick of claim 10 wherein said means for providing a tactile indication of an orientation of said toothpick includes at least one groove disposed in said main body.

12. The toothpick of claim 10 wherein said means for providing a tactile indication of an orientation of said toothpick includes at least one geometric shape.

13. The toothpick of claim 10 wherein said means for providing a tactile indication of an orientation of said toothpick includes at least one groove or at least one geometric shape disposed in said main body, and wherein said at least one groove or said at least one geometric shape is either cut, impressed, molded, burned, or etched into said main body.

14. The toothpick of claim 10 wherein said raised or recessed geometric shape is disposed on a same side of said main body as is said sloping curvature.

15. The toothpick of claim 10 wherein said raised or recessed geometric shape is disposed on an opposite side of said main body that said sloping curvature is disposed.

16. A toothpick, comprising:
    (a) a main body that includes a longitudinal length and wherein said main body includes a first end and an opposite second end, and wherein said main body is not hollow, and wherein, during manufacture of said toothpick, said first end includes a conical shape, thereto, and wherein, during further manufacture, additional material is removed from said conical end;
    (b) wherein, during said further manufacture, a sloping curvature that begins a predetermined distance away from said first end at an upper exterior surface of said main body is provided, and wherein said sloping curvature progressively extends deeper into said main body toward an opposite bottom surface of said conical shaped first end as said sloping curvature progressively extends toward said first end, wherein said sloping curvature terminates at said first end and at said opposite bottom surface of said conical shaped first end to provide a termination of said first end, and wherein said additional material that is removed from said first end includes all of conical shaped first end that is disposed above said sloping curvature, and wherein said sloping curvature extends across a width of said main body, and wherein said termination of said first end is disposed below a longitudinal center axis of said main body, and wherein said termination of said first end includes an arcuate shape that extends across a width of said main body along where said sloping curvature and said opposite bottom surface of said conical shaped first end intersect, and wherein said arcuate shape includes an edge that extends along an entire length of said said termination of said first end, wherein said termination of said first end of said toothpick includes a rounded end, and wherein an entire length of said edge includes said arcuate shape, and wherein said edge is able to enter a gingival sulcus without puncturing a tissue that said edge contacts at a base of said gingival sulcus; and (c) a raised or recessed geometric shape that provides a tactile indication of an orientation of said toothpick, said means for providing a tactile indication disposed on said exterior surface of said main body.

\* \* \* \* \*